United States Patent
Rand et al.

(10) Patent No.: US 6,735,271 B1
(45) Date of Patent: May 11, 2004

(54) ELECTRON BEAM COMPUTED TOMOGRAPHIC SCANNER SYSTEM WITH HELICAL OR TILTED TARGET, COLLIMATOR, AND DETECTOR COMPONENTS TO ELIMINATE CONE BEAM ERROR AND TO SCAN CONTINUOUSLY MOVING OBJECTS

(75) Inventors: Roy E. Rand, Palo Alto, CA (US); Jonathan Harman, Pacifica, CA (US); Douglas P. Boyd, Hillsborough, CA (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 351 days.

(21) Appl. No.: 09/728,481

(22) Filed: Nov. 28, 2000

(51) Int. Cl.[7] .................................. H05G 1/60
(52) U.S. Cl. ............................. 378/4; 378/15
(58) Field of Search .................. 378/4, 15, 137, 378/901, 10

(56) References Cited

U.S. PATENT DOCUMENTS 4,944,448 A * 7/1990 Peschmann et al. ..... 228/173.2
5,247,556 A * 9/1993 Eckert et al. .................. 378/21

* cited by examiner

Primary Examiner—Drew A. Dunn
Assistant Examiner—Courtney Thomas
(74) Attorney, Agent, or Firm—McAndrews, Held & Malloy, Ltd.; Peter J. Vogel; Michael A. Dellapenna

(57) ABSTRACT

A scanning electron beam computed tomographic system eliminates axial offset between target and detector by disposing the target, collimator, and detector such that active portions of the target and detector are always diametrically opposite each other. This result is achieved by providing a helical target, collimator, and detector, or by providing planar target, collimator, and detector components that are inclined relative to the vertical axis such that active portions of the target and detector are always diametrically opposite each other. Either configuration eliminates cone beam error and the necessity to correct for same. Further, the system can provide multi-slice scanning of an object that is in constant motion at a critical velocity, without having to interpolate data. Conventional helical scanning may still be undertaken. Detector elements can be disposed axially to improve signal/noise ratio and to produce a cone beam cancellation effect.

15 Claims, 8 Drawing Sheets

$\theta_T = -90°$      $\theta_T = 0$      $\theta_T = 90°$

ELECTRON BEAM COMPUTED TOMOGRAPHIC SCANNER SYSTEM WITH HELICAL OR TILTED TARGET, COLLIMATOR, AND DETECTOR COMPONENTS TO ELIMINATE CONE BEAM ERROR AND TO SCAN CONTINUOUSLY MOVING OBJECTS

FIELD OF THE INVENTION

The present invention relates generally to scanning electron beam computed tomography X-ray systems, and more particularly to eliminating cone beam error in images produced by such systems, and thus the need to correct for such error, and to providing such systems with an option to make multi-slice scanning of moving objects without requiring that acquired data be interpolated.

BACKGROUND OF THE INVENTION

A century ago, mathematician J. Radon demonstrated that a two-dimensional slice of a three-dimensional object may be reproduced from the set of all of its projections. Computed tomography (CT) X-ray systems generate a set of X-ray beam projections through an object to be examined. The resultant detected X-ray data are computer processed to reconstruct a tomographic image-slice of the object.

Conventional CT systems subject the object under examination to one or more pencil-like X-ray beams from all possible directions in a plane. The X-ray data may be generated in fan beam format (as is the case for the present invention), or in parallel beam format. In a fan beam system, the X-rays radiate from a source and are collected in a fan. By contrast, in a parallel beam system the X-rays are all parallel within a view. In either system, a view is one projection of the object onto the detectors, and a scan is a collection of all of the views.

In a fan beam scanning electron beam system such as described in U.S. Pat. No. 4,521,900 to Rand, or U.S. Pat. No. 4,352,021 to Boyd, an electron beam is produced by an electron gun and is accelerated downstream along the z-axis of an evacuated chamber. Further downstream a beam optical system deflects the electron beam about 30° into a scanning path, with azimuthal range typically about 210°. The deflected beam is then focused upon a suitable target, typically a large arc of tungsten material, which produces a fan beam of X-rays.

The emitted X-rays penetrate an object (e.g., a patient) that is disposed along the z-axis and lying within a so-called reconstruction circle. X-ray beams passing through the object are attenuated by various amounts, depending upon the nature of the object traversed (e.g., bone, tissue, metal). One or more X-ray detectors, disposed on the far side of the object, receive these beams and provide signals proportional to the strength of the incoming X-rays.

Typically the output data from the detectors are processed using a filtered back-projection algorithm. Detector data representing the object scanned from many directions are arranged to produce image profiles for each scan direction. Since the X-rayed object is not homogeneous, these profiles will vary in intensity with the amount of radiation detected by the various detectors on the various scans. The convoluted data from the various projections are then superimposed, or back-projected, to produce a computed tomographic image of the original object. The thus processed data are used to produce a reconstructed image of a slice of the object, which image may be displayed on a video monitor.

Systems similar to what is described in the above patents to Rand or Boyd are manufactured by Imatron, Inc., located in South San Francisco, Calif. These systems are termed "short scan" because the views used for reconstructing an object image cover 180° plus the fan beam angle (about 30°), e.g., about 210° total, rather than a full 360°. In a scanning electron beam CT system, the 210° angle implies that the target and detector must overlap, which is to say occupy the same space azimuthally.

In prior art systems this problem has been solved by using a parallel planar target and detector that are separated axially. In such systems, the X-ray detectors also span 180° plus the fan angle, and define a first plane that is orthogonal to the z-axis. The source of the X-rays scans or travels within a second plane, also orthogonal to the z-axis, but not coincident with the first plane. As the X-ray fan rotates around the target, the central ray from the target to the detector describes a shallow cone rather than an ideal plane. Thus, although ideally reconstruction creates an image in a plane perpendicular to the z-axis using views acquired within that plane, in practice the presence of a cone angle in prior art systems results in each acquired view being inclined rather than perpendicular to the z-axis. This "cone beam" effect causes data sets acquired from axially non-invariant objects to be self-inconsistent, which results in image artifacts that degrade image quality and can produce false diagnoses in medical applications.

Unless the cone beam geometry is accounted for by using data from more than one axial position, cone beam error results. The result is a reconstructed image that includes unwanted cone beam artifacts that appear as streaks in the reconstructed, displayed image. In general, cone beam artifacts can be reduced in part only at the expense of scanning contiguous or overlapping slices, and interpolating the data from adjacent slices. U.S. Pat. No. 5,406,479 (1995) to Harman, assigned to Imatron, Inc., assignee herein, describes a method of reconstructing data acquired from a fan beam system such that cone beam error is substantially reduced. However efficient as the Harman technique is, it still requires data processing steps that would not be required if cone beam error could simply be eliminated as an error source. Applicants refer to and incorporate by reference U.S. Pat. No. 5,406,479 to Harman, U.S. Pat. No. 4,521,900 to Rand, and U.S. Pat. No. 4,352,021 to Boyd.

Another problem associated with prior art scanning electron beam CT systems occurs in so-called helical or spiral scanning. In this mode of operation, an object is continuously scanned while being moved at a constant velocity in the axial direction. During scanning, azimuthal and axial motions of the X-ray fan become mixed such that further interpolations must be performed on the resultant data before planar images can be reconstructed. The requirement to perform data reconstruction slows down the reconstruction process, reduces system throughput, and adds to the processing requirements of the overall system.

Thus in a scanning electron beam CT system, there is a need for a method and system to substantially eliminate cone beam error, and thus a need to compensate or correct for such error. Preferably the resultant system should exhibit higher quality images with reduced false diagnoses in medical applications. Finally, the reduction in data processing realizable by such systems should make possible scanning of continuously moving objects with image reconstruction substantially in real-time.

The present invention provides such a system.

SUMMARY OF THE INVENTION

A scanning electron beam computed tomographic system eliminates axial offset between target and detector, and resultant cone beam error, by disposing the target, detector, and collimator elements such that active regions of the target and detector are always diametrically opposite each other. This result is obtained by using a helical target, helical collimator, and helical detector. Alternatively, the target, collimator, and detector may be planar, but tilted or inclined about the vertical axis or other transverse axis to approximate an ideal helical configuration.

Eliminating the need to correct for cone beam error and, in some modes of operation, eliminating the need to interpolate data, reduces system cost, reduces computational overhead, and can increase system throughput. Higher quality images are produced, and the decreased data processing makes possible scanning of continuously moving objects and reconstructing acquired images substantially in real-time.

In the helical target, detector, collimator embodiment, the pitch of the helices is sufficient to separate the target and detector axially in overlap regions. The electron beam spot is scanned around the helical target at constant angular velocity to produce an X-ray fan whose axial position moves at a constant velocity Vcrit along the scanner axis.

In a first, helical, mode of operation, the object being scanned is moved at this same, critical, constant velocity Vcrit such that the object slice being scanned remains fixed with respect to the object. In this mode, discrete planar slices are scanned, without cone beam error and without need for data interpolation. A second mode may be used for objects that are moved at non-critical velocity. In this mode helical scanning similar to what is practiced with conventional scanning electron beam CT systems is possible. Data interpolation is needed to produce images, but there is no cone beam error, or need for cone beam correction. In a third mode, step mode scanning is used, in which data interpolation is needed, but no cone beam error or cone beam correction is required.

In the helical or tilted embodiments thus far described, detectors in the detector array were disposed in the azimuthal direction, but not the axial direction. In an alternative embodiment, an array of detectors that includes detector elements disposed in the axial (z-axis) direction is disclosed. Such a multiple axial detector array can provide for more efficient use of X-ray dosage for narrow slices, which increases signal/noise ratio and decreases total scan time. Further, the cone beam effect may be made self-cancelling for images obtained from the various detectors.

Other features and advantages of the invention will appear from the following description in which the preferred embodiments have been set forth in detail in conjunction with the accompanying drawings.

DESCRIPTION OF THE PREFERRED EMBODIMENTS

Figure 1A:
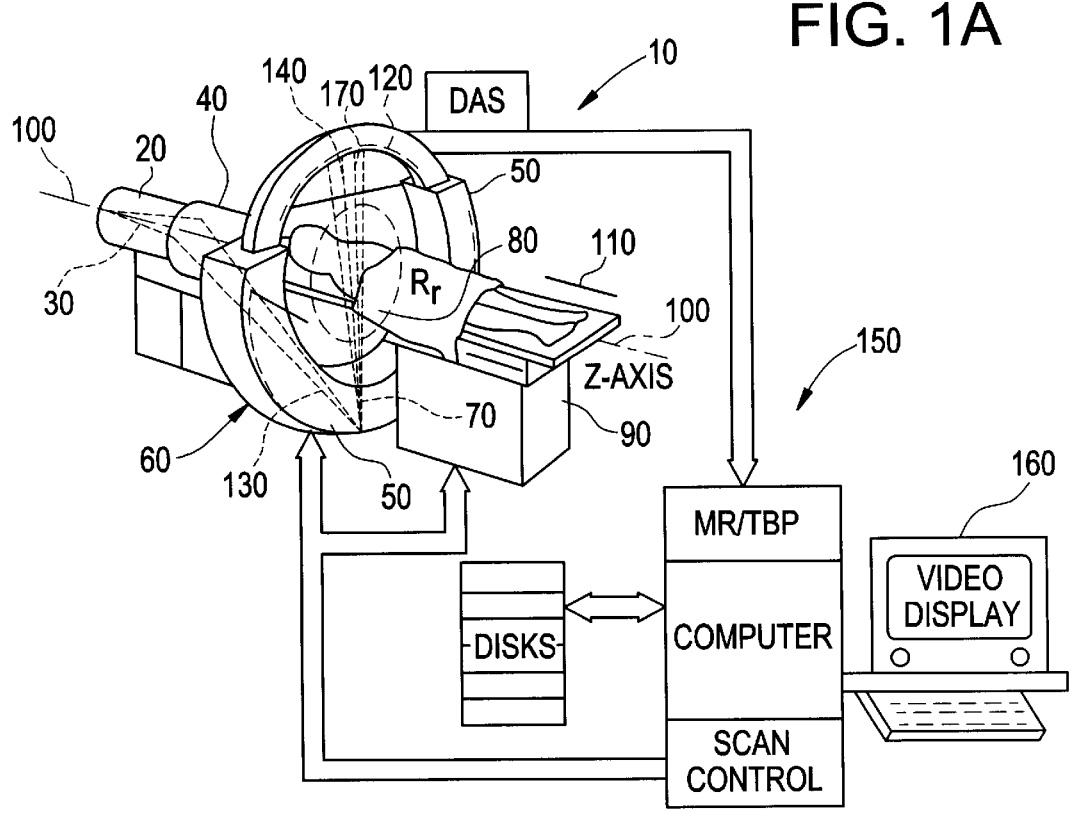
FIG. 1A depicts a fan beam scanning electron beam computed tomography system, according to the present invention.

FIG. 1A depicts a scanning electron beam computed tomography (CT) system 10 according to the present invention. System 10 includes a vacuum housing chamber 20 wherein an electron beam 30 is generated and caused by a beam optics assembly 40 to scan a circular target 50 located within chamber 20's front lower portion 60. Upon being struck by the electron beam, which typically scans 210° or so, the target emits a moving fan-like beam of X-rays 70 that pass through a region of a subject 80 (e.g., a patient or other object) within the reconstruction radius Rr. Patient or object 80 typically lies on a couch 90 that is movable along the system z-axis 100 at a chosen velocity, as indicated by arrow 110. These rays then register upon a region of a detector array 120 located generally diametrically opposite. System 10 typically includes a collimator system that.includes collimator elements 130 adjacent target 50, and collimator elements 140 adjacent detector array 120. The detector array outputs data to a computer processing system 150 that processes and records the data to produce an image of a slice of the subject 80 on a video monitor 160. Computer system 150 can also control operation of system 10, including moving couch 90 along z-axis 100 at a desired velocity.

As will be described more fully herein, collimators 130, 140, target 50, and detector array 120 are preferably each helical or, if planar, are tilted or inclined about a vertical axis to approximate an ideal helical configuration. The goal is to provide active portions of the target 50 and detector array 120 that are always diametrically opposite from each other such that there is no cone beam effect, and no cone beam artifacts on the image produced by system 10. This is achieved in the present invention by causing central rays 170 of the emitted X-ray fans to be perpendicular to the system z-axis 100. This is achieved, but at the expense of a small twist of the X-ray fan about its central ray, but in most cases this twist is negligible and requires no correction.

Figure 1B:
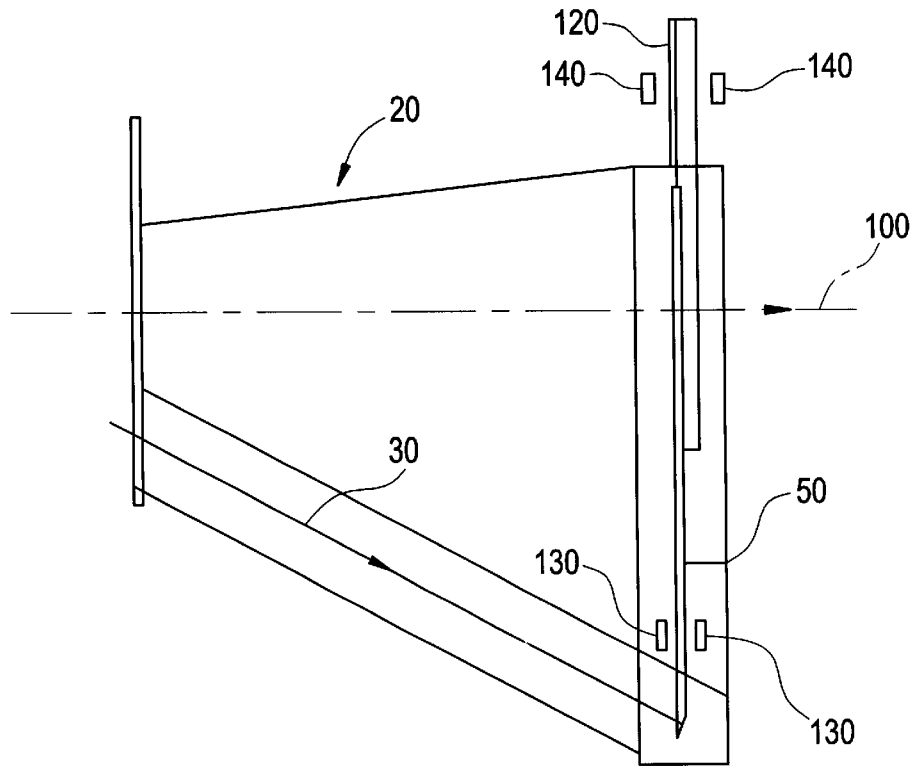
FIG. 1B is a cross-section of a portion of the system of FIG. 1A, according to the present invention.
Figure 1C:
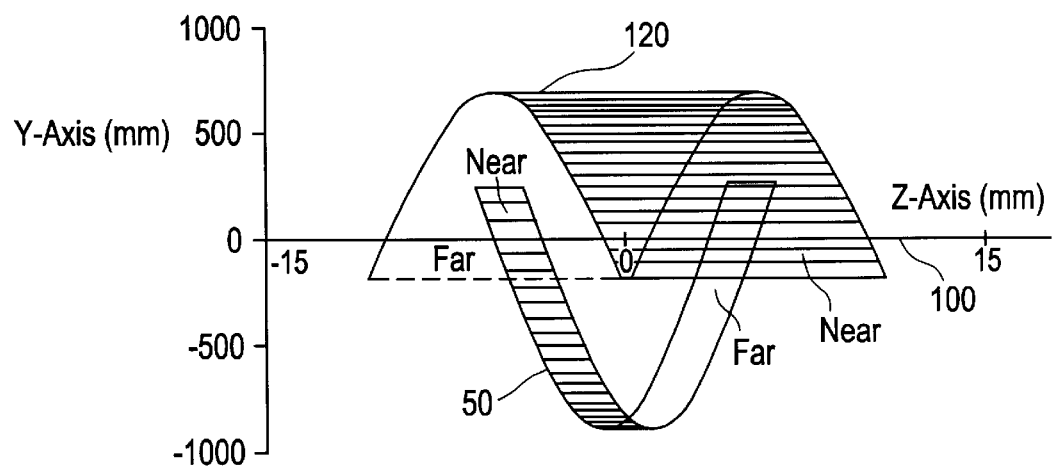
FIG. 1C is an expanded side view portion of FIG. 1B, depicting the double helix formed between the target and detector, with the axial z-axis scale expanded 100:1, according to the present invention.
Figure 1D:
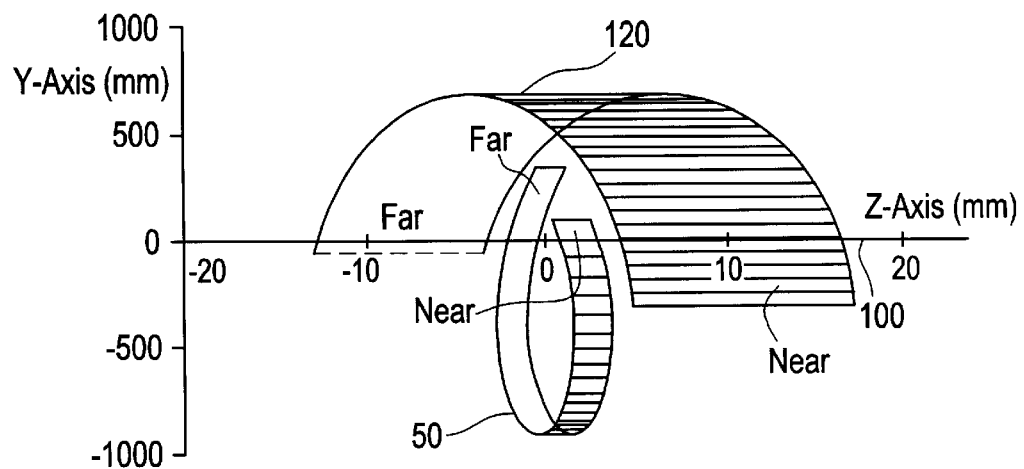
FIG. 1D is a perspective view of the target and detectors, according to the present invention.

FIG. 1B is a simplified cross-section of the right-hand portion of system 10, showing the spatial relationship between electron beam 30, target 50, and detector 120. As shown in FIG. 1B, FIG. 1C and FIG. 1D, target 50 and detector 120 form an opposing double helix. In practice the width of an acquired image slice and the axial limits of the X-ray fans emitted from target 50 will be limited by the geometry of the collimating system elements 130, 140. If necessary, the detector itself can perform the collimation function. The configuration of FIG. 1B will have active portions of the target and detector always opposite each other, with the result that the cone beam error is eliminated.

The electron beam scanning components in system 10 cause the X-ray source, e.g., the electron beam spot formed by the scanning electron beam 30 on target 50, to traverse along target 50 at a constant speed, whose axial component is denoted Vcrit. Thus, the intersection of the central rays 170 of the emitted X-ray fans with system axis 100 moves at a constant speed along that axis. If the patient or object 80 being scanned is moved at the same constant speed, Vcrit, it is seen that the X-ray fans will always scan the same slice of the object.

The preferred implementation of the present invention will provide helical target, detector, and if present collimator elements, although the tilted planar element configuration described above may also be used. The object or patient to be scanned will be moved with a constant velocity along the system z-axis, either continuously or in selected increments. For medical applications, such movement functionality is normally available in that a couch 90 under control of computer system 150 will be present. Industrial scanners could be similarly configured, but a more useful mode of operation would be to scan objects carried on a continuous conveyor belt that passes through system 10. In some applications it might even be advantageous to have the objects to be scanned stationary, and to move system 10 over the objects.

FIG. 1C is an expanded side view portion of FIG. 1B, depicting the double helix formed between target 50 and detector 120. For ease of understanding, the z-axis scale is expanded 100:1. It is apparent from FIG. 1C that the goal of providing active regions of the target and detector that are always opposite each other has been met. FIG. 1D is an explanatory perspective view of the target 50 and detector 120.

Figure 2A:
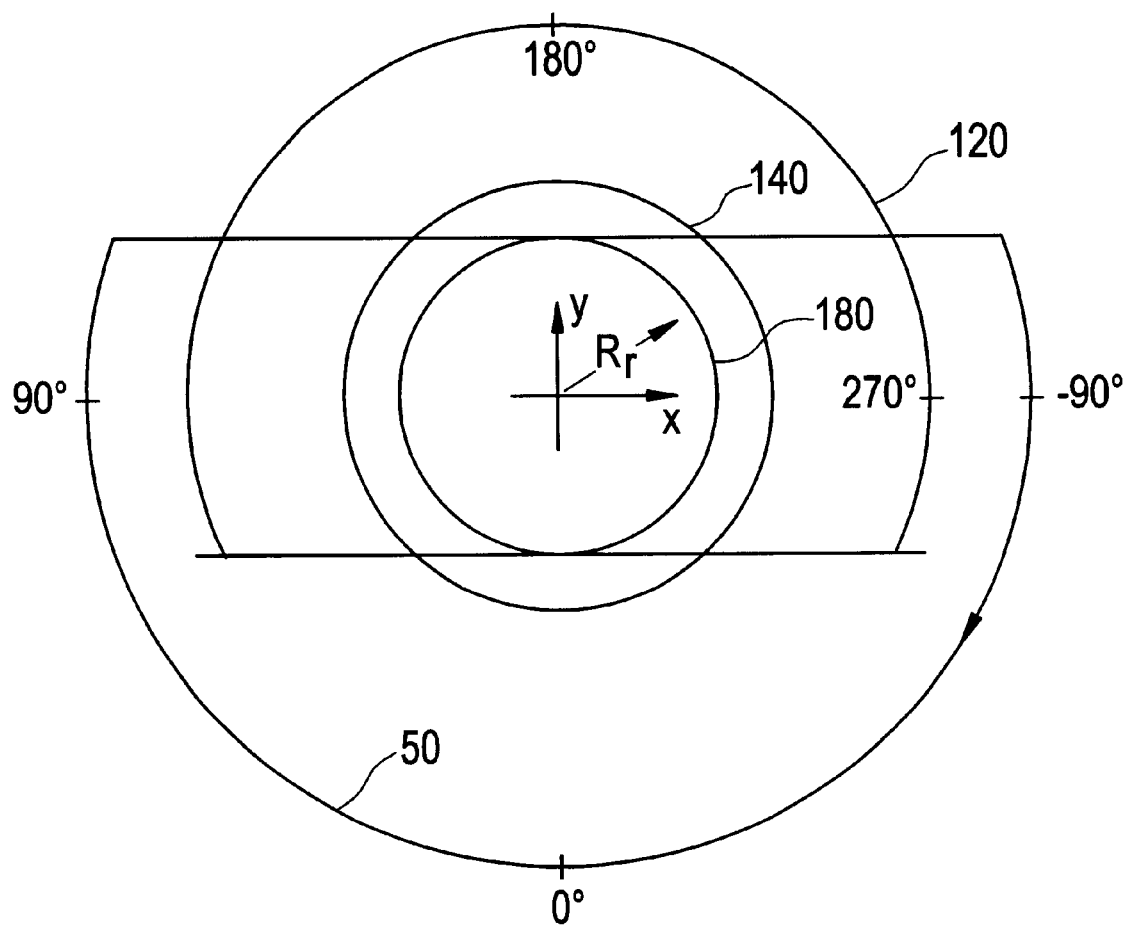
FIG. 2A is an axial view depicting the relationship between the target, the detector, the collimator, and a reconstruction circle, according to the present invention.

FIG. 2A is an axial view along z-axis 100 showing the relationship between target 50, detector 120, and a reconstruction circle 180 having maximum radius Rr. It is understood that all portions of the object 80 to be scanned must fit within the area defined by the reconstruction circle. In FIG. 2A, the electron beam is shown being swept along target 50 in a clockwise direction. FIG. 2A also shows the orientation of the various azimuth angles used herein.

Figure 2B:
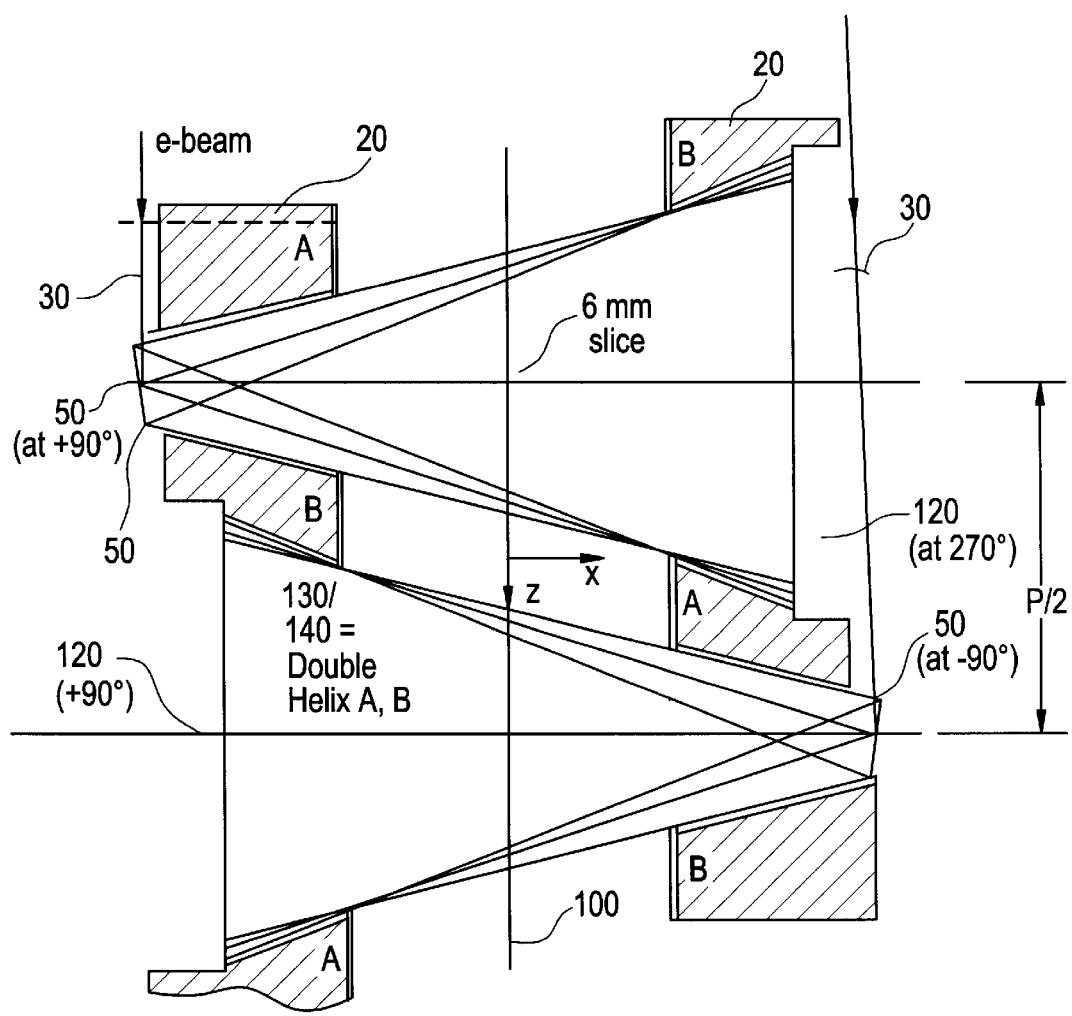
FIG. 2B is a section of system 10 through the horizontal plane, with the axial z-axis scale expanded 100:1, according to the present invention.

FIG. 2B depicts a section through the horizontal plane of system 10, with the z-axis 100 scale expanded 100:1 for the sake of clarity. The figure indicates a slice width of about 6 mm, and depicts relative component positions for azimuthal target angles of −90° and +90°. Shown cross-hatched in FIG. 2B are lead shielding portions of housing 20 that are necessary to appropriately confine the X-ray beams, whose paths are also shown. In the configuration shown, the slice width (here 6 mm) is defined by post-collimation, in which the collimator forms a second but asymmetric double helix (denoted A, B). A pre-collimation slot would be dimensioned so as not to interfere with the emitted X-ray fan. Preferably the geometrical pitch of all helices is the same. In FIG. 2B, a half-pitch length separates the two fans.

In practice, target 50 is made primarily of tungsten, a rather rigid and not easily machinable material that can complicate the practical realization of a true helical target. However as shown by analysis presented later herein, if a tilted planar target is used, the magnitude of the maximum error in the X-ray source axial position is about 0.5 mm for a 3 mm slice width. Normally in scanning electron beam CT systems the target will be tilted with respect to the radial direction by a small angle, perhaps 12°. Thus, even in the worst case, the radial position of the X-ray beam spot need be moved by only 2.4 mm to achieve the correct axial position. This radial error in X-ray source position is much less than the radial length of the beam spot itself, and can be tolerated.

Although fabricating a truly helical target can be challenging, fabricating helical detectors is relatively straightforward. Detector housings are normally quite flexible and in fact must be constrained to lie in a plane. Therefore in the preferred embodiment, detector housings may be constrained to follow a helix of pitch about equal to the width of the detector housing itself.

Helical collimators would be implemented as a double helix of strips of an X-ray absorbing material, e.g., lead or tantalum. The helices may be attached to a Mylar cylinder similar to those used in conventional electron beam CT systems.

An alternative configuration may be implemented in which the target, collector, and collimator are not formed as true helices. In the alternative embodiment, the target, collector, and collimator may be formed planar, but with their planes tilted slightly relative to each other about the vertical y-axis such that the actual axial positions of the components for any diametrically opposite points are the same. The amount of tilt is selected such that the axial position of each tilted component (target, collector, collimator) coincides with its ideal helix at any three points. The easiest such configuration would be to select coincidence at target angles of −90°, 0°, and +90°. A section through the horizontal plane in such a system would be precisely as shown in FIG. 2B for the helical case. The principal difference between the simplified planar element configuration and a true helical configuration is that axial speed of the X-ray source is no longer constant for the planar configuration. However in most practical applications, the axial position error at any given time would be substantially less than the slice width. The implementation of the tilted target configuration may be simplified by slewing the direction of object motion about the vertical y-axis, instead of tilting the target. A tilted detector is still required. In principle, the axis of tilt can be in any direction perpendicular to the scanner axis but the vertical axis is preferred.

Figure 3:
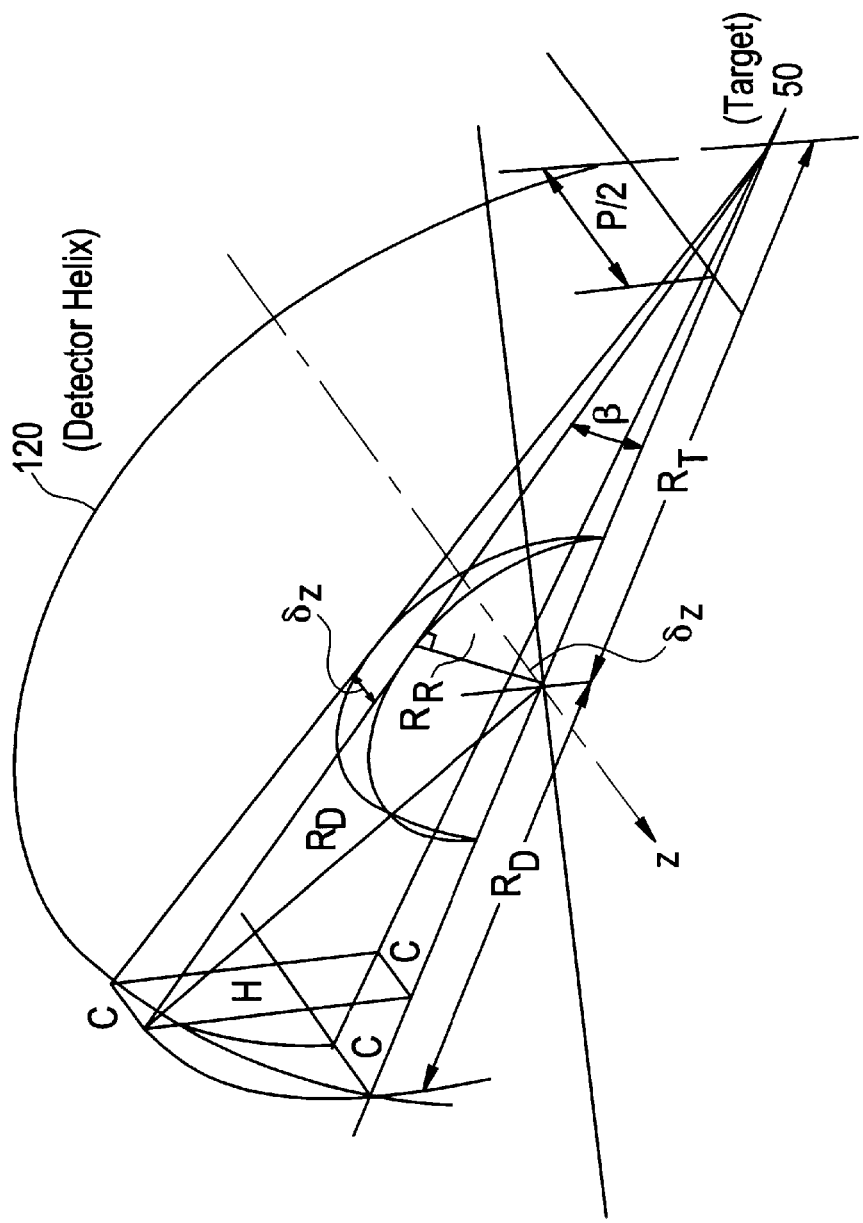
FIG. 3 depicts tilting of an X-ray fan about the radial direction and nomenclature used herein, according to the present invention.

An analysis of the effect of tilt in an X-ray fan from the target due to a helical detector will now be described for a helical configuration. As shown by FIG. 3, in a helical configuration the X-ray fan is tilted, disadvantageously, about the radial direction. For ease of illustration, FIG. 3 assumes that the detector itself forms the collimator. In general, the collimator will determine X-ray fan geometry, and the detector radius would actually be replaced by the collimator radius. The following nomenclature will be used in the analysis that will now be given.

| | |
|---|---|
| Rt | target radius |
| Rd | detector radius |
| Rr | reconstruction circle radius |
| DθT | total target angle |
| θT | target angle (−0.5 DθT ≦ θT < +0.5 DθT range) |
| θD | detector angle |
| β | source fan half-angle |
| P | true pitch of all helices |
| S | effective pitch of imaging system |
| W | slice width |

-continued

| | |
|---|---|
| H | defined by FIG. 3 |
| C | defined by FIG. 3 |
| δZ | axial displacement of edge of source fan at a distance Rt/cos(β) from the source |
| DZ | axial error in slice center position (for tilted configuration) |
| φ | source fan tilt angle |
| Ts | scan time |
| ISD | inter-scan delay |
| Vcrit | axial object speed at which no data interpolation is required |
| V(contig) | object speed for continuous slices |
| Vmax(interp) | maximum object speed for "good" interpolation |
| Z(t) | axial position of slice center at time t, where t = 0 at θT = 0 |
| π | 3.14159 . . . |

It follows that $$\delta Z = \frac{C \cdot Rr}{H \cdot \cos(\beta)} 15$$

where $$C = \frac{P}{2 \cdot \pi} \cdot \arcsin\left(\frac{H}{Rd}\right)$$

and $$H = (\sqrt{Rt^2 - Rr^2} + \sqrt{Rd^2 - Rr^2}) \cdot \sin(\beta)$$

where $$\sin(\beta) = \frac{Rr}{Rt}$$

Further, $$S = \frac{P}{2} \cdot \frac{D\theta T}{\pi} \cdot \frac{Ts + ISD}{Ts}$$

where $$\phi = \frac{\delta Z}{Rr}$$

$$Vcrit = \frac{\frac{P}{2} \cdot \frac{D\theta T}{\pi}}{Ts}$$

$$Z(t) - Z(0) = Vcrit \cdot t = \frac{P}{2} \cdot \frac{\theta T}{\pi}$$

$$Z\left(\frac{\pm Ts}{2}\right) - Z(0) = \pm \frac{P}{4} \cdot \frac{D\theta T}{\pi}$$

$$V(contig) = \frac{W}{Ts + ISD}$$

$$Vmax(interp) = \frac{V(contig)}{2}$$

In practice there are limits on the pitch of the helices, and the effective pitch. Consideration of the geometry of FIG. 2B and of the amount of X-ray shielding that might be required in a practical scanning system suggests that the minimum helical pitch is probably limited by the requirement that Pmin/2 lie within a range of about (W+1.5 mm) to about (3·W/2). In the examples calculated below it will be assumed that Pmin=3·W.

Maximum pitch is defined to be the pitch at which the offset δZ equals half the slice width. It is assumed that image artifacts due to fan tilt will be small and correctable (if necessary) up to this maximum pitch limit. It follows then that:

$$Pmax = \frac{\pi \cdot W \cdot H \cdot \cos(\beta)}{Rr \cdot \arcsin\left(\frac{H}{Rd}\right)}$$

The following calculations are to be considered as exemplary only and not limiting upon the scope of the present invention. The design constraints are based upon parameters of a commercially available scanning system, such as the model C-150 sold by Imatron, Inc. (assignee herein) of South San Francisco, Calif.

| | |
|---|---|
| Rt | 900 mm |
| Rd | 675 mm |
| Rr | 250 mm |
| DθT | 210° |
| W | 3.0 mm |
| Ts | 100 ms |
| ISD | 16 ms |
| β | 16.13° |
| V(contig) | 25.9 mm/sec |
| Vmax(interp) | 12.9 mm/sec |

The minimum pitch helix is characterized as follows:

| | |
|---|---|
| Pmin | 9.0 mm |
| Smin | 6.09 mm |
| ΔZmin | 0.595 mm |
| φmin | 0.136° |
| Vcrit | 52.5 mm/sec |

In practice, for a minimum pitch helix the tilt of the X-ray source fan will be only about 25% of the cone beam angle typical for an Imatron C-150 type collimator system. For this reason, artifacts resulting from fan tilt will not be large.

The maximum pitch helix may be characterized as follows:

| | |
|---|---|
| Pmax | 22.70 mm |
| Smax | 15.36 mm |
| δZmax | 1.5 mm |
| φmax | 0.344° |
| Vcrit | 132.4 mm/sec |

The relational dependency of fan tilt on reconstruction circle radius Rr may be explained by rewriting the earlier equation for δZ as follows:

$$\delta Z = \frac{P}{2 \cdot \pi} \cdot \frac{Rr \cdot Rt}{\sqrt{Rt^2 - Rr^2}} \cdot \frac{\arcsin\left(\frac{H}{Rd}\right)}{H}$$

Figure 4A:
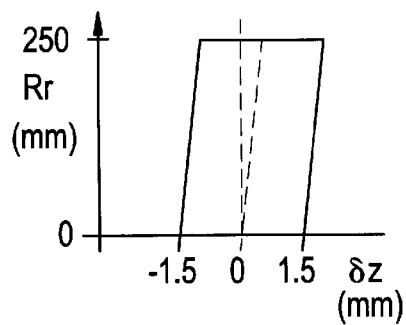
FIG. 4A shows a slice profile for a helical embodiment of the present invention.

FIG. 4A presents a slice profile plot of δZ (as expressed above) vs. Rr for a helical configuration in which W=3 mm with minimum pitch in the design example. Note that as Rr approaches zero, then $$\delta Z \rightarrow \frac{P}{2\cdot\pi}\cdot\frac{Rr}{Rd}$$

Consider now an embodiment in which the target and detector are tilted about $$\delta Z = \frac{C\cdot Rr}{H\cdot\cos(\beta)}$$

a vertical y-axis such that the extreme positions of the target and detector each lie at the same axial positions $Z=\pm(P/4)$. Further, in the tilted configuration, a straight line joining the point $\theta T$ on the target to the point $\theta D=\theta T+180°$ on the detector will pass through and be perpendicular to the system z-axis.

The effect of the shape of the X-ray fan and axial position error will now be described. It is still correct that: however, $$C = \frac{P}{4}\cdot\left[\sin\left\{\theta T + \arcsin\left(\frac{H}{Rd}\right)\right\} - \sin(\theta T)\right]$$

where $$\theta T = D\theta T\cdot\frac{t}{Ts}$$

At $\theta T=0$, $$C = \frac{P}{4}\cdot\frac{H}{Rd}$$

At $\theta T=\pm 90°$, $$C = \pm\frac{P}{4}\cdot\left[\sqrt{1-\left(\frac{H}{Rd}\right)^2} - 1\right]$$

At the center of the slice, axial position is given by:

$$Z(t) - Z(0) = \frac{P}{4}\cdot\sin(\theta T)$$

Thus at the slice center position, the axial error DZ(t) is given by:

$$DZ(t) = \frac{P}{4}\cdot\left[\sin(\theta T) - \frac{2\cdot\theta T}{\pi}\right]$$

As in the case of a helical configuration, in a tilted embodiment the practical minimum pitch is determined by the necessity to shield the back of the detector array from X-rays. In calculating maximum pitch, it is assumed that $\delta Z<W/2$ and that $DZ<W/2$. The maximum value of $\delta Z$ occurs at $\theta T=0$, where $$\delta Zmax = \frac{Pmax}{4}\cdot\frac{Rr}{Rd\cos(\beta)}$$

The maximum value of DZ occurs at $\theta T=\arccos(2/\pi)=50.46°$, where $DZmax=(Pmax/4)\cdot 0.2105$.

In the exemplary design described using parameters typical for an Imatron C-150 type scanner system, the limiting dimension for Pmax remains $\delta Zmax$. The error DZ can be corrected in practice by adjustment of the electron beam spot radius on the target, as was described with respect to a helical configuration of the present invention, e.g., by moving the X-ray beam spot radially by a small amount.

Consider the following design example for a tilted embodiment, in which the same parameters used earlier for an Imatron C-150 system will still be assumed.

| | | |
|---|---|---|
| Minimum tilt (pitch) | Pmin | 9.0 mm |
| | Smin | 6.09 mm |
| | $\delta$Zmin | 0.867 mm at $\theta T = 0$ |
| | $\phi$min | 0.199° |
| | Vcrit | 52.5 mm/sec |
| | DZmin | 0.474 mm |
| Maximum tilt (pitch) | Pmax | 15.56 mm |
| | Smax | 10.53 mm |
| | $\delta$Zmax | 1.5 mm at $\theta T = 0$ |
| | $\phi$max | 0.344° |
| | Vcrit | 90.8 mm/sec |
| | DZmax | 0.819 mm |

Figure 4B:
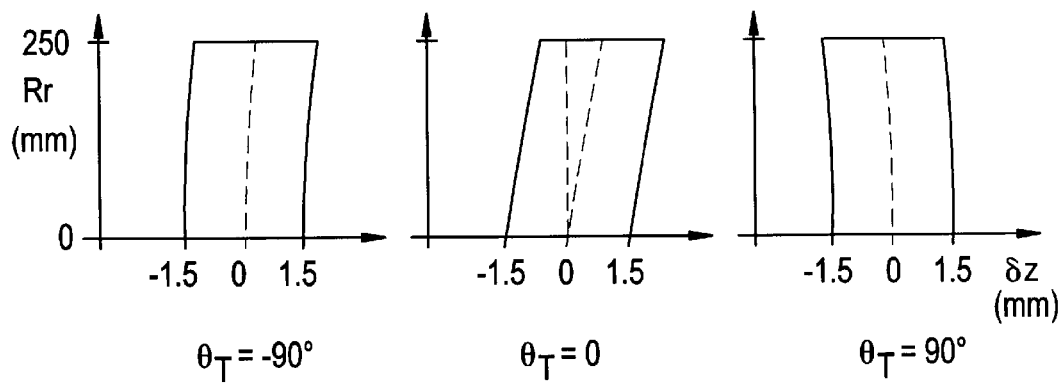
FIG. 4B shows slice profiles for a tilted embodiment of the present invention.

Dependence of the X-ray fan shape upon the reconstruction circle radius Rr will now be described for a tilted configuration of the present invention with reference to the slice profiles shown in FIG. 4B. FIG. 4B plots $\delta Z$ as a function of reconstruction radius Rr for the minimum tilt dimensions at target angles $\theta T=-90°$, $\theta T=0$ and $\theta T=90°$. In this plot, $\delta Z$ is again given by:

$$\delta Z = \frac{C\cdot Rr}{H\cdot\cos(\beta)}$$

At extreme angles, errors in the fan geometry are only of second order in Rr. In conventional prior art electron beam CT systems, a similar error occurs at all angles and is always considered negligible.

Various modes of operation may be defined for the present invention, and in all of the modes to be described, there is no cone beam error, and thus no need to correct for cone beam errors.

In a step mode, contiguous or overlapping slices are scanned with the object stationary for each slice. In contrast to the equivalent mode in a conventional scanning electron beam CT system, the data must be interpolated. The step mode represents the zero speed limit of a conventional electron beam CT helical mode. FIGS. 5A–5H are useful in understanding interpolation requirements for step mode operation and general helical mode operations for prior art electron beam CT systems, and for the present invention. In the scan profiles of FIGS. 5A–5H, V represents scanner velocity relative to the object being scanned, and in each case second order effects of scan profiles are ignored.

Figure 5A:
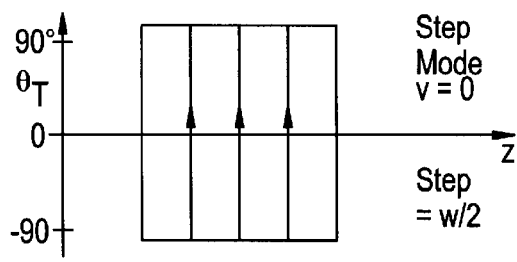
FIGS. 5A–5H depict scan profiles in the object frame of reference for various scanner velocities, for prior art systems, and for the present invention.
Figure 5B:
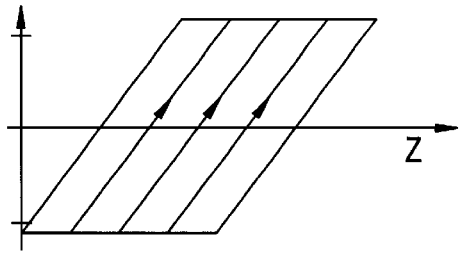

FIG. 5A shows scan profiles for a prior art system in step mode for zero velocity, during each scan, whereas FIG. 5B shows scan profiles for the present invention used in step mode. Note in FIG. 5B that contiguous or overlapping slices may be scanned, and in contrast to what is shown in prior art FIG. 5A, data interpolation will have to be made even for contiguous slices (but of course no cone beam correction is required).

Figure 5C:
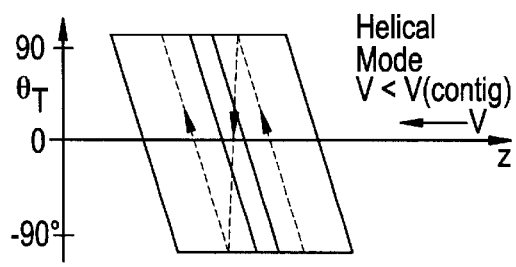
Figure 5D:
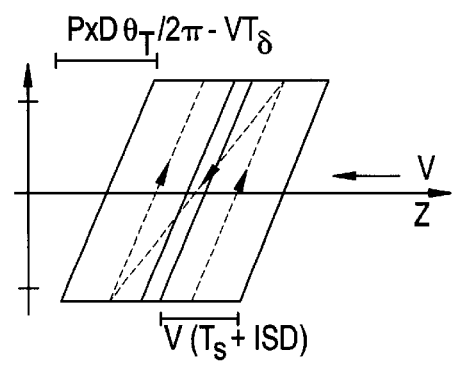
Figure 5E:
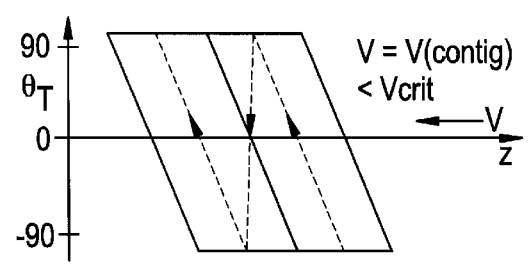
Figure 5F:
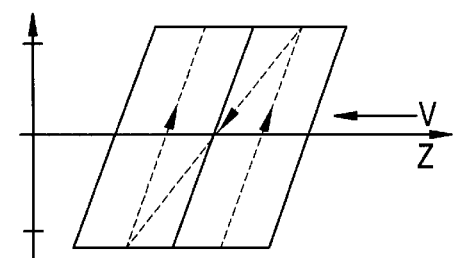

Now consider the present invention used in helical mode, in which the object speed is constant but $\leq$V(contig). This mode will provide contiguous or overlapping slices, and interpolation of data will be necessary, just as it is with prior art helical scanning. (Of course in the present invention, no cone beam correction is required.) For best results, adjacent slices should overlap by not less than half the slice width. The interpolation formulae (known to those skilled in the relevant art) are the same as in the prior art case with object speed replaced by (object speed−Vcrit). FIGS. 5C and 5E are scan profiles for sub-contiguous velocity for a prior art system in helical mode, whereas FIGS. 5D and 5F are scan profiles for sub-contiguous velocity for the present invention in helical mode. In this mode of operation, note that contiguous or overlapping slices result, and that for prior art systems (FIGS. 5C, 5E) and for the present invention (FIGS. 5D, 5F) data interpretation is required. However in contrast to what is shown in prior art FIGS. 5C and 5E, no cone beam correction is required for the sub-contiguous velocity operation of the present invention in helical mode.

Figure 5G:
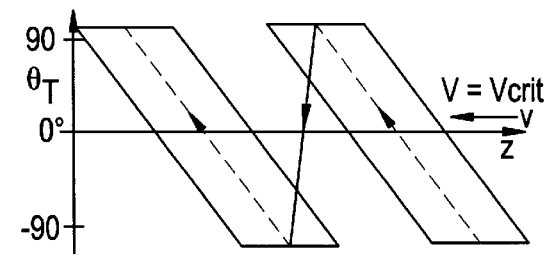
Figure 5H:
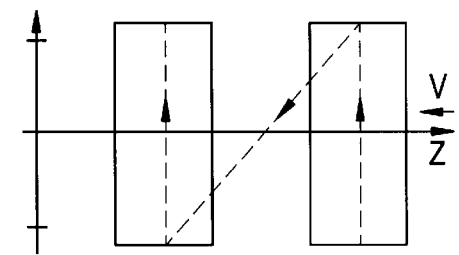

In a critical speed mode, the speed of object or patient 80 along z-axis 100 is made equal to the axial speed (Vcrit) of the X-ray source. In this mode, equally spaced slices are scanned, without the necessity for data interpolation. The slices are not contiguous but are separated by about one slice width. FIG. 5G is a scan profile for a prior art system at the critical object velocity defined for the present invention, and FIG. 5H is a scan profile for the present invention at critical velocity. In each set of figures, equally spaced slices are produced, adjacent slices being separated by about one slice width. However in stark contrast to the data represented by prior art FIG. 5G, the data in FIG. 5H needs no data interpolation at all, and of course needs no cone beam correction.

Note that none of the modes of the present invention is physically possible for mechanical CT scanners. Only in the electron beam CT scanner is it possible to return the X-ray source from the end of the scan at one axial position to the start of the next scan at a different axial position in a very short interscan delay time.

Table 1, below, summarizes the comparisons between prior art electron beam CT systems, and the present invention described above.

TABLE 1

|  | Prior Art Systems | Present Invention |
| --- | --- | --- |
| Cone beam effect | Must correct for cone beam error | No cone beam effect |
| Fan tilt effect | No fan tilt effect | In extreme cases, fan tilt correction may be required |
| Step Mode - Contiguous Slices | No interpolation required | Interpolation required |
| Step Mode - Overlapping slices | Interpolation required | Interpolation required |
| Helical Mode V ≦ V(contig) | Interpolation required | Interpolation required |
| Helical Mode V = Vcrit | Not generally useful | Discrete slices obtained No interpolation required |

Figure 6A:
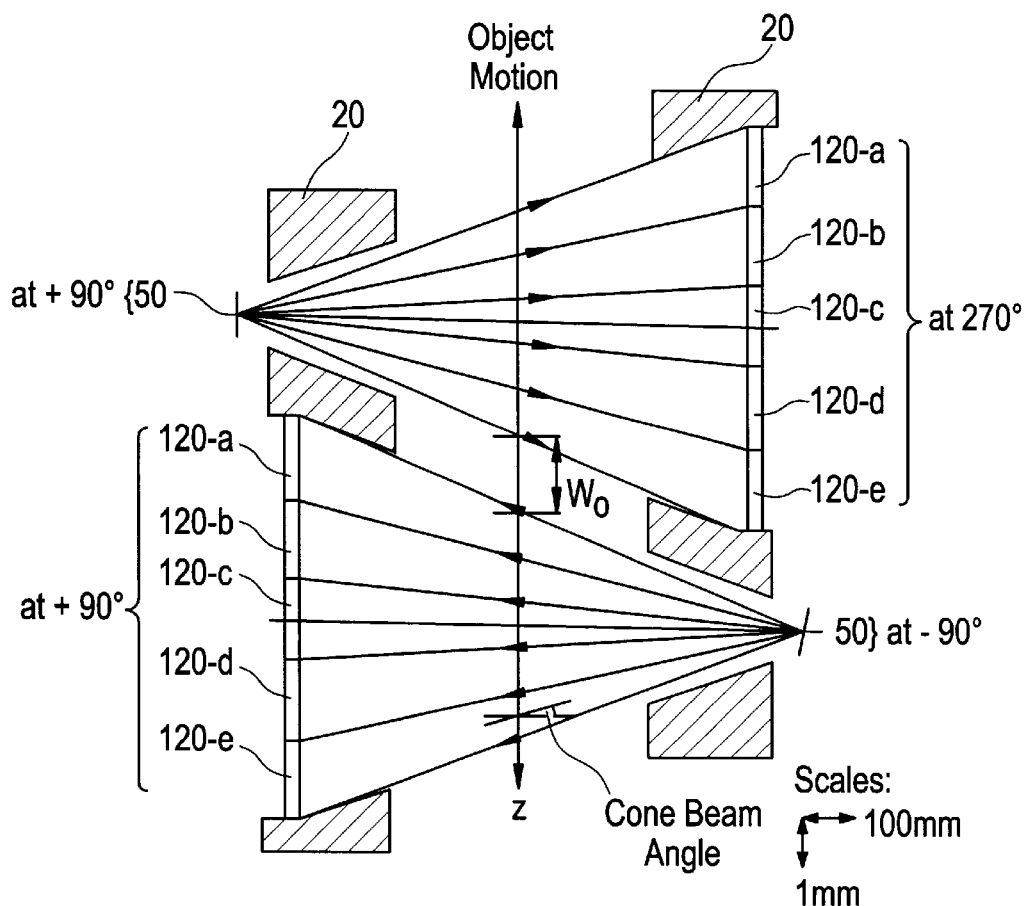
FIG. 6A is a section through the horizontal plane of a system 10 having axially disposed detector elements, with the axial z-axis scale expanded 100:1, according to the present invention.
Figure 6B:
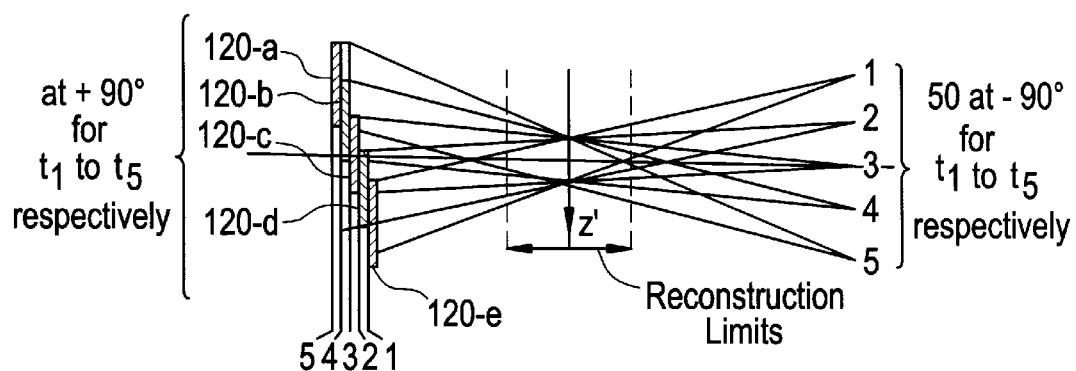
FIG. 6B depicts target and detector element positions at times $t_1$, through $t_5$, for the configuration of FIG. 6A.

Turning now to FIGS. 6A and 6B, an embodiment of the present invention is depicted in which detector array 120 includes detector elements that are disposed axially, along the z-axis, in addition to azimuthally disposed elements, as have been assumed in the above descriptions.

FIG. 6A is shown relative to the scanner system 10 frame of references, with five axially-adjacent detector elements (denoted 120-a, . . . 120-e) depicted.

The horizontal scale is amplified 100 times relative to the vertical scale in this depiction, for ease of understanding. FIG. 6A is somewhat similar to FIG. 2B, except that the detector array is split into multiple elements in the z-axis direction. In the configuration shown, these detector elements form the slice-defining collimators. In the exemplary FIGS. 6A and 6B, five 1.5 mm slices are scanned at once. Cone beam effects, although less severe than in a conventional prior art scanning electron beam CT system, will be present for a stationary object in all slices except the center slice.

FIG. 6B is shown relative to the object frame of reference and depicts, at the left hand portion of the figure, positions of detector elements at +90° at equally spaced times: $t_1$, $t_2$, $t_3$, $t_4$, and $t_5$. The right hand portion of the same figure shows −90° target positions at the same five times, the numbers 1,2,3,4 and 5 being shorthand for the five times.

For each sweep of the electron beam along the target, the X-ray dose for each separate slice is the same as would be the case for a single slice of the same width. Assume now that the object or patient to be scanned is moved in the negative z-axis direction (in the scanner system frame of reference) at a steady speed of one slice width per sweep period (including the interscan delay time). In the object frame of reference shown in FIG. 6B, each slice is scanned with the target in five different z' positions, and with five different cone beam angles. Advantageously the data from these five samples can be added or averaged with the result that the five different cone beam angle Values and associated corrections average to zero.

In this example, the first effect of the motion will increase X-ray dosage by a factor of five, which will decrease noise in the reconstructed image, thus improving the signal/noise ratio. A second effect of the patient motion is to cancel linear cone beam effects. Cancellation occurs since for every data sample with a given cone beam angle, there will be matching sample with an opposite cone beam angle. Thus, cone beam correction is not always necessary with multiple detectors disposed in the axial direction. However data so obtained will still suffer from a defect that the z' position of each slice is a function of the X-ray source or the target angle. However this is a normal situation with helical scanning, and data for a slice that is fixed in z' is obtained by interpolating the data.

Consider now the practical limitations on the number of axially-disposed detector elements and the reconstruction circle radius for the above-described embodiment of FIGS. 6A and 6B. The number (N) of detector elements or slices than can be scanned simultaneously may be thought of in terms of the maximum reconstruction circle radius (Rr) for a given value of N. For good image quality it is preferred that Rr be limited by requiring that at radius Rr, slice displacements due to fan angle tilt and due to cone beam effect each be less than half the slice width. In the expressions that follow, limits on Rr are calculated for a pure helical geometry.

For convenience of the reader, some previously defined expression are repeated below:

| | |
| --- | --- |
| Rt | target radius |
| Rd | detector radius |
| Rr | reconstruction circle radius |
| N | number of axially-disposed detector elements or number of simultaneous slices |
| P | true pitch of all helices (detector and target) |
| W | slice width |
| W0 | distance along z-axis required for shielding (see FIG. 6A) |
| δZ | axial displacement of edge of source fan at a distance Rt/cos(β) from the source |
| Ts | scan time |
| ISD | inter-scan delay |

-continued

| | |
|---|---|
| Z' | axial position in object frame of reference |
| θT | target angle |
| Vcrit | axial object speed at which no data interpolation is required for N = 1 |

The X-ray fan tilt limit follows from the geometric relationship $P/2 = N \cdot W + W0$. Assuming that $\delta Z < W/2$, in the limit of small fan angle $\beta$.

$$Rr < \frac{\pi \cdot Rd}{2 \cdot \left(N + \frac{W0}{W}\right)}$$

The cone beam limit is obtained as follows. The maximum cone beam angle for the extreme slices is given by:

$$\frac{(N-1) \cdot W}{2 \cdot Rt}$$

Assuming that at radius Rr cone beam displacement must be less than W/2, it follows that:

$$Rr < \frac{Rt}{(N-1)}$$

Consider a design example in which eight detector elements are present, which elements can be coupled together to produce N=4, N=2, or N=1 slices. Let Rt=900 mm, Rd=725 mm, and W0=2.5 mm.

As shown by Table 2 below, in all cases, the helical fan tilt effect gives a lower limit for Rr than the cone beam effect. Further, the above example provides a useful medical scanner, in which 0.75 mm slices would be limited to use in scanning the human head, while 1.5 mm and wider slices could be used to scan the head and chest.

TABLE 2

| N | W (mm) | Rrmax (tilt) (mm) | Rrmax (cone) (mm) |
|---|---|---|---|
| 8 | 0.75 | 100 | 129 |
| 4 | 1.5 | 200 | >250 |
| 2 | 3.0 | >250 | >250 |
| 1 | 6.0 | >250 | >250 |

Understandably practical limits exist on scanning speed and X-ray dosage. For N elements, the speed at which the object to be scanned must be moved to increase the dosage by a factor of N compared with a single slice scanner is W/(Ts+ISD). In the above design example, with W=1.5 mm, and (Ts+ISD)=116 ms, the required object speed is 12.9 mm/sec.

Note that 12.9 mm/sec is also the speed that requires the least interpolation of the data, since only the variation of Z' with θT must be corrected, as in the simplest prior art helical scanning case. Note too that 12.9 mm/sec is substantially less than the critical speed Vcrit, which is only useful for N=1, and for which no data interpolation is required.

For greater dose in the example configuration, object speeds less than 12.9 mm/sec are possible, but the slower speeds would introduce extra data interpolation requirements, needed to correct the slice Z' position. In certain applications, speeds greater than 12.9 mm/sec may also be possible.

To recapitulate the various embodiments, in all modes of operation the present invention can eliminate or at least substantially eliminate cone beam error, and the computationally intensive need to compensate for such error. Ideally the invention would be used in helical mode at the critical velocity Vcrit, in which case not only is no cone beam correction required, but no data interpolation is required. Image processing for multiple images is sped up, and the computational cost of the overall system can be reduced. At object velocities less than about 0.5·Vcrit, interpolation correction is required at a level about equal to that in prior art helical mode electron beam CT systems. A potential disadvantage to the present invention is that unlike prior art systems, a single slice of a stationary object cannot be scanned in isolation unless the whole scanner is moved. Stated differently, either helical scanning or step mode scanning, e.g., scanning of overlapping adjacent slices with a stationary object, is necessary. In the multiple z-axis detector array element configuration, signal/noise ratio can be substantially improved and/or total scan time reduced, with the possibility of cancellation of cone beam error.

It will be appreciated that the present invention has utility beyond medical and scientific applications. Other applications of the present invention can range from industrial use including quality inspection and control, to security applications in which it may be necessary to rapidly detect the presence of objects or materials concealed within a package traveling on a conveyor.

Modifications and variations may be made to the disclosed embodiments without departing from the subject and spirit of the invention as defined by the following claims.

What is claimed is:

1. In a scanning electron beam computed tomographic system in which an electron beam is scanned across a target with a constant velocity to emit a fan beam of X-rays some of which X-rays may pass through an area defined by a reconstruction radius and having an object therein to be detected by a detector array, a method of eliminating cone beam error, comprising the following steps:
    (a) configuring and disposing said target and said detector array such that active regions of said target and said detector array are always diametrically opposite from each other;
        wherein step (a) includes providing a planar target and a planar detector array and tilting said target and said detector array relative to a transverse axis that may include a vertical axis of said system to approximate a true helix configuration.

2. In a scanning electron beam computed tomographic system in which an electron beam is scanned across a target with a constant velocity to emit a fan beam of X-rays some of which X-rays may pass through an area defined by a reconstruction radius and having an object therein to be detected by a detector array, a method of eliminating cone beam error, comprising the following steps:
    (a) configuring and disposing said target and said detector array such that active regions of said target and said detector array are always diametrically opposite from each other;
    (b) moving said object along a z-axis of said system with an object velocity equal to a critical velocity Vcrit during helical mode operation of said system;
        wherein discrete equally-spaced slices of said object may be scanned without need to interpolate scan data acquired by said system.

3. The method of claim 2, wherein said object is moved with said velocity Vcrit relative to a stationary said system.

4. The method of claim 2, wherein said system is moved with said velocity Vcrit relative to a stationary said object.

5. The method of claim 4, wherein said object is moved with velocity less than approximately half Vcrit relative to a stationary said system.

6. The method of claim 4, wherein said system is moved with said velocity less than approximately half a constant critical velocity Vcrit relative to a stationary said object.

7. In a scanning electron beam computed tomographic system operated in helical mode in which an electron beam is scanned across a target with a constant velocity to emit a fan beam of X-rays some of which X-rays may pass through an area defined by a reconstruction radius and having an object therein to be detected by a detector array, a method of acquiring scan data without a need to interpolate said data, the method comprising the following steps:

(a) configuring and disposing said target and said detector array such that active regions of said target and said detector array are always diametrically opposite from each other;

(b) providing relative movement of said object to said system along a z-axis of said system at a critical velocity Vcrit;

wherein equally spaced object slices are acquired without need to interpolate said data.

8. The method of claim 7, wherein step (a) includes providing a helical shaped said target and providing a helical shaped said detector array.

9. The method of claim 7, wherein step (a) includes providing a planar target and a planar detector array and tilting said target and said detector array relative to a transverse axis that may include a vertical axis of said system to approximate a true helix configuration.

10. The method of claim 7, wherein step (a) includes providing a detector array including elements disposed along an axial axis of said system.

11. A scanning electron beam computed tomographic system in which cone beam error is eliminated, comprising:

a helical shaped target;

a helical shaped detector array;

said target and said detector array disposed such that active regions of said target and active regions of said array are always diametrically opposite one another;

means for generating and sweeping an electron beam across said target with a constant velocity to emit a fan beam of X-rays some of which X-rays may pass through an area defined by a reconstruction radius and having an object therein to be detected by said detector array;

means for moving said object relative to a z-axis of said system with an velocity less than or equal to a critical velocity Vcrit;

wherein in helical mode operation of said system, if said velocity=Vcrit, scan data representing equally spaced slices of said object are obtained without need to interpolate said data.

12. The system of claim 11, wherein said means for moving has a characteristic selected from a group consisting of (i) said object is moved and said system is stationary, and (ii) said system is moved and said object is stationary.

13. A scanning electron beam computed tomographic system in which cone beam error is eliminating, comprising:

a planar target tilted with respect to a transverse axis that may include a vertical axis of said system to approximate a true helix;

a planar detector array tilted with respect to the same axis of said system to approximate a true helix;

said target and said detector array disposed such that active regions of said target and active regions of said array are always diametrically opposite one another; and means for generating and sweeping an electron beam across said target with a constant velocity to emit a fan beam of X-rays some of which X-rays may pass through an area defined by a reconstruction radius and having an object therein to be detected by said detector array.

14. The system of claim 13, further including:

means for moving said object relative to a z-axis of said system with a velocity less than or equal to a critical velocity Vcrit;

wherein in helical mode operation of said system, if said velocity=Vcrit scan data representing equally spaced slices of said object are obtained without need to interpolate said data.

15. The system of claim 13, wherein said detector array includes elements displaced along an axial axis of said system.

* * * * *

UNITED STATES PATENT AND TRADEMARK OFFICE
CERTIFICATE OF CORRECTION

PATENT NO. : 6,735,271 B1
APPLICATION NO. : 09/728271
DATED : May 11, 2004
INVENTOR(S) : Rand et al.

It is certified that error appears in the above-identified patent and that said Letters Patent is hereby corrected as shown below:

col. 7, lines 30-34, please delete " $H = \left( \sqrt{Rt^2 - Rr^2} + \sqrt{Rt^2 - Rr^2} \right) \bullet \sin(\beta)$ "

and insert -- $H = \left( \sqrt{Rt^2 - Rr^2} + \sqrt{Rt^2 - Rr^2} \right) \bullet \sin(\beta)$ -- col. 9, lines 7-10, please delete " $\delta Z = \dfrac{C \bullet Rr}{H \bullet \cos(\beta)}$ " and insert on line 18 after the word "that"

and before the word "however" -- $\delta Z = \dfrac{C \bullet Rr}{H \bullet \cos(\beta)}$ --

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,735,271 B1 | Page 1 of 1 |
| APPLICATION NO. | : 09/728481 | |
| DATED | : May 11, 2004 | |
| INVENTOR(S) | : Rand et al. | |

It is certified that error appears in the above-identified patent and that said Letters Patent is hereby corrected as shown below:

col. 7, lines 30-34, please delete " $H = \left( \sqrt{Rt^2 - {}^{Rr\,2}} + \sqrt{Rt^2 - {}^{Rr\,2}} \right) \bullet \sin(\beta)$ "

and insert -- $H = \left( \sqrt{Rt^2 - Rr^2} + \sqrt{Rt^2 - Rr^2} \right) \bullet \sin(\beta)$ -- col. 9, lines 7-10, please delete " $\delta Z = \dfrac{C \bullet Rr}{H \bullet \cos(\beta)}$ " and insert on line 18 after the word "that"

and before the word "however" -- $\delta Z = \dfrac{C \bullet Rr}{H \bullet \cos(\beta)}$ --

This certificate supersedes Certificate of Correction issued August 15, 2006.

Signed and Sealed this

Tenth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 6,735,271 B1 Page 1 of 1
APPLICATION NO. : 09/728481
DATED : May 11, 2004
INVENTOR(S) : Rand et al.

It is certified that error appears in the above-identified patent and that said Letters Patent is hereby corrected as shown below:

Col. 16, claim 13, line 17, please delete "eliminating" and insert --eliminated--

Signed and Sealed this

Twenty-ninth Day of May, 2007

JON W. DUDAS
*Director of the United States Patent and Trademark Office*